United States Patent
Matsusue et al.

(10) Patent No.: US 11,479,658 B2
(45) Date of Patent: Oct. 25, 2022

(54) FILM-FORMING COMPOSITION AND FILM (71) Applicant: Shin-Etsu Chemical Co., Ltd., Tokyo (JP)

(72) Inventors: Shintaro Matsusue, Joetsu (JP); Takuya Yokosawa, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 79 days.

(21) Appl. No.: 17/196,213

(22) Filed: Mar. 9, 2021

(65) Prior Publication Data
US 2021/0284823 A1     Sep. 16, 2021

(30) Foreign Application Priority Data
Mar. 13, 2020    (JP) .............................. JP2020-044608

(51) Int. Cl.
*C08L 1/28*    (2006.01)

(52) U.S. Cl.
CPC ......... *C08L 1/284* (2013.01); *C08L 2205/025* (2013.01); *C08L 2205/03* (2013.01)

(58) Field of Classification Search
CPC . C08L 1/284; C08L 2205/025; C08L 2205/03
See application file for complete search history.

(56) References Cited

U.S. PATENT DOCUMENTS 4,389,393 A * 6/1983 Schor ................... A61K 9/2054
514/180
5,756,123 A 5/1998 Yamamoto et al.

FOREIGN PATENT DOCUMENTS

| EP | 3181126 A1 | 6/2017 |
| GB | 1494868 A | 12/1977 |
| JP | H08208458 A | 8/1996 |
| JP | 2010270039 A | 12/2010 |
| WO | 2008050209 A1 | 5/2008 |

OTHER PUBLICATIONS

Extended European Search Report corresponding to European Patent Application No. 21161863.2 (7 pages) (dated Jul. 26, 2021).

* cited by examiner

*Primary Examiner* — Jeffrey C Mullis
(74) *Attorney, Agent, or Firm* — Myers Bigel, P.A.

(57) ABSTRACT

There is provided a film-forming composition, including: a first water-soluble cellulose ether (WSCE) having a viscosity at 20° C. of 2.5 to 45 mPa·s, a second WSCE having a viscosity at 20° C. of 6.0 to 50.0 mPa·s, a third WSCE having a viscosity at 20° C. of 4.5 to 15.0 mPa·s, each viscosity being determined in a 2% by mass aqueous solution, and a solvent, wherein the first WSCE is selected from four members of hydroxypropyl methyl celluloses Ia and Ib in Group I and hydroxypropyl methyl cellulose IIa and methyl cellulose IIb in Group II, the second WSCE is the same member as that of the first WSCE, provided that the substitution degree(s) of the second WSCE may be the same as or different from that of the first WSCE, and the third WSCE is selected from members in a Group different from the Group of the first WSCE.

20 Claims, 1 Drawing Sheet

FILM-FORMING COMPOSITION AND FILM

CROSS-REFERENCE TO RELATED APPLICATION

This U.S. nonprovisional application claims priority to Japanese Application No. 2020-044608 filed Mar. 13, 2020, the entire contents of which are incorporated herein by reference.

BACKGROUND OF THE INVENTION

1. Field of the Invention

The invention relates to a composition for forming a film and the film.

2. Related Art

A water-soluble cellulose ether such as methyl cellulose (hereinafter also referred to as "MC") and hydroxypropyl methyl cellulose (hereinafter also referred to as "HPMC") are widely used in pharmaceutical or food applications. Among examples of the water-soluble cellulose ether, HPMC is particularly excellent in solubility in water, and forms a tough and flexible film when the aqueous HPMC solution is dried. Since the formed film has high transparency and is excellent in gas barrier properties and moisture barrier properties, it is widely used as a film-forming base material for coating tablets and granules, and as a base material for a film formulation and a hard capsule.

A hard capsule is a conventionally widely used dosage form because it is easy to formulate and can mask the taste and odor of the capsule content. Gelatin has been widely used as a base material for the hard capsule. However, since gelatin is derived from animals, there is a risk of infection such as bovine spongiform encephalopathy (BSE). In addition, the gelatin tends to crack when the moisture content decreases. For this reason, a hard capsule produced from the gelatin as a base material must contain a large amount of moisture. As a result, a drug may be deactivated due to the moisture.

On the other hand, the water-soluble cellulose ether is derived from a plant, and even if the water content in the film is lowered, the strength of the film does not decrease. Thus, the water-soluble cellulose ether has no problem described above.

A hard capsule produced from a water-soluble cellulose ether as a base material has many advantages as described above, but it has problems that solubility in water is low compared with hard capsules produced from gelatin as a base material and release of the hard capsule content is delayed.

For the purpose of improving the solubility of a hard capsule produced from a water-soluble cellulose ether as a base material, it is described in PH 08-208458A that a film composition for a capsule comprises 18 to 28 parts by weight of HPMC having a viscosity at 20° C. of from 2.4 to 5.4 cSt, as determined in a 2% aqueous solution, as a base material; 0.01 to 0.1 parts by weight of carrageenan as a gelling agent; and 0.05 to 0.6 parts by weight of potassium ions, calcium ions or both as a gelling aid. It is also described in JP 2010-270039A that a film for a hard capsule comprises hypromellose and at least one selected from the group consisting of monosaccharides, disaccharides and starches.

SUMMARY OF THE INVENTION

However, a film formed from relatively low-viscosity HPMC, such as HPMC described in JPH 08-208458A, is fragile and has insufficient strength. An additive such as monosaccharides, disaccharides and starches, as described in JP 2010-270039A, has a possibility of inducing rapid microbial growth.

In view of the above circumstances, an object of the invention is to provide a film-forming composition capable of forming a film having both good solubility and good strength, as well as the film.

As a result of extensive studies to achieve the above object, the inventors have found a film excellent in solubility and strength can be formed by combining the same types of first and second water-soluble cellulose ethers having different viscosities with a third water-soluble cellulose ether which is of the same type as but the different substitution degree from those of the first and second water-soluble cellulose ethers, or with a third polymer which is of a different type from those of the first and second water-soluble cellulose ethers, and thus has completed the invention.

In an aspect of the invention, there is provided a composition for forming a film, the composition comprising:

a first water-soluble cellulose ether having a viscosity at 20° C. of from 2.5 to 4.5 mPa·s, as determined in a 2% by mass aqueous solution;

a second water-soluble cellulose ether having a viscosity at 20° C. of from 6.0 to 50.0 mPa·s, as determined in a 2% by mass aqueous solution;

a third water-soluble cellulose ether having a viscosity at 20° C. of from 4.5 to 15.0 mPa·s, as determined in a 2% by mass aqueous solution; and a solvent;

wherein the first water-soluble cellulose ether is selected from four members:

two members both in Group I:

hydroxypropyl methyl cellulose Ia having a degrees of substitution (DS) of methoxy groups of from 1.10 to 1.60 and a molar substitution (MS) of hydroxypropoxy groups of from 0.10 to 0.33, and     hydroxypropyl methyl cellulose Ib having a degrees of substitution (DS) of methoxy groups of from 1.80 to 2.00 and a molar substitution (MS) of hydroxypropoxy groups of from 0.20 to 0.34, and   two members both in Group II:

hydroxypropyl methyl cellulose IIa having a degree of substitution (DS) of methoxy groups of from 1.70 to 2.00 and a molar substitution (MS) of hydroxypropoxy groups of from 0.10 to 0.18, and     methyl cellulose IIb having a degree of substitution (DS) of methoxy groups of from 1.60 to 2.00, wherein the second water-soluble cellulose ether is the same member as that of the first water-soluble cellulose ether, provided that DS and if present, MS of the second water-soluble cellulose ether may be the same as or different from the DS and if present, MS of the first water-soluble cellulose ether, and wherein the third water-soluble cellulose ether is selected from members in a Group different from the Group of the first water-soluble cellulose ether.

In another aspect of the invention, there is provided a film comprising the first water-soluble cellulose ether, the second water-soluble cellulose ether, and the third water-soluble cellulose ether.

According to the invention, a film excellent in strength and solubility can be obtained.

DETAILED DESCRIPTION OF THE PREFERRED EMBODIMENTS

Figure 1:
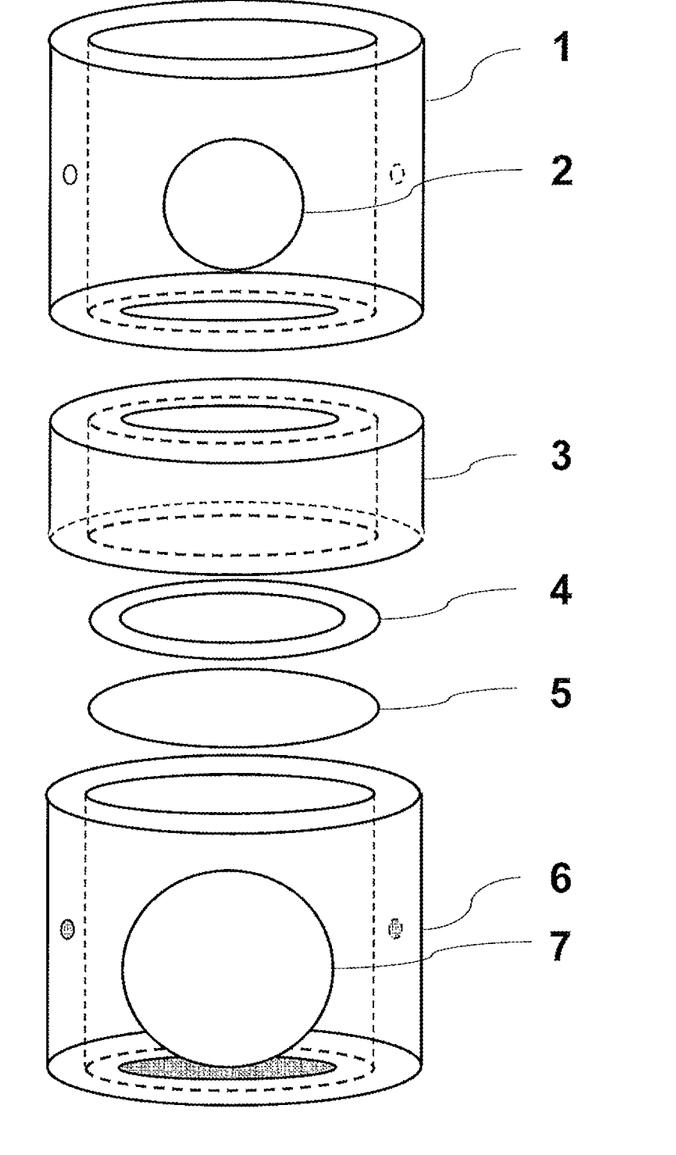
The FIGURE shows a sample holder to be used for measuring the dissolution time of a film.

1. Film-Forming Compostion
(1) Water-Soluble Cellulose Ethers

First, a water-soluble cellulose ether to be used in a composition for forming a film will be described.

A first water-soluble cellulose ether, a second water-soluble cellulose ether, and a third water-soluble cellulose ether, all of which are nonionic, are used for the composition for forming a film.

<Viscosity of Water-Soluble Cellulose Ether>

The strength and solubility of the film of the water-soluble cellulose ether are correlated with the viscosity at 20° C. of the 2% by mass aqueous solution of the water-soluble cellulose ether. When the viscosity of the water-soluble cellulose ether is too low, the solubility of the film is improved, but the strength of the film is lowered. On the contrary, when the viscosity of the water-soluble cellulose ether is too high, the strength of the film is improved, but the solubility of the film is lowered. Accordingly, the viscosities of the first, second and third water-soluble cellulose ethers to be used in the composition for forming a film must be within the ranges described later.

The viscosity at 20° C. of the 2% by mass aqueous solution of the first water-soluble cellulose ether is from 2.5 to 4.5 mPa·s, preferably from 2.8 to 4.5 mPa·s, more preferably from 3.0 to 4.5 mPa·s. When the viscosity is less than 2.5 mPa·s, the strength of the film decreases, causing problems such as easy cracking of the film. When the viscosity is more than 4.5 mPa·s, it becomes difficult to obtain good solubility of the film.

The viscosity at 20° C. of the 2% by mass aqueous solution of the second water-soluble cellulose ether is from 6.0 to 50.0 mPa·s, preferably from 6.0 to 40.0 mPa·s, more preferably from 6.0 to 35.0 mPa·s. When the viscosity is less than 6.0 mPa·s, since the content of the cellulose ether having a low viscosity increases, the strength of the film decreases, causing problems such as easy cracking of the film. When the viscosity is more than 50.0 mPa·s, it is difficult to obtain good solubility of the film.

The viscosity at 20° C. of the 2% by mass aqueous solution of the third water-soluble cellulose ether is from 4.5 to 15.0 mPa·s, preferably from 4.5 to 12.0 mPa·s, more preferably from 4.5 to 9.0 mPa·s. When the viscosity is less than 4.5 mPa·s, there are problems such as the decreased strength and easy cracking of the film. When the viscosity is more than 15.0 mPa·s, it is difficult to obtain good solubility of the film.

In addition, the difference between the viscosity at 20° C. of a 2% by mass aqueous solution of the first water-soluble cellulose ether and that of the second water-soluble cellulose ether (i.e., (the viscosity at 20° C. of the 2% by mass aqueous solution of the second water-soluble cellulose ether)-(the viscosity at 20° C. of the 2% by mass aqueous solution of the first water-soluble cellulose Ether)) is preferably 2.0 mPa·s or more, more preferably from 2.5 to 45.0 mPa·s, and still more preferably from 2.8 to 30.0 mPa·s, from the viewpoint of solubility of the film.

Since the viscosity at 20° C. of the 2% by mass aqueous solution of each of the first, second and third water-soluble cellulose ethers is less than 600 mPa·s, the viscosity may be determined using the Ubbelohde type viscometer in accordance with the viscosity measurement by capillary tube viscometer of the General Tests in the Japanese Pharmacopoeia Seventeenth Edition.

<Type and Substitution Degree of Water-Soluble Cellulose Ether>

Next, the type and substitution degree of the water-soluble cellulose ether to be used in the composition for forming a film will be described.

The first water-soluble cellulose ether is selected from four members in Groups I and II. The second water-soluble cellulose ether is the same member as that of the first water-soluble cellulose ether, provided that DS and if present, MS of the second water-soluble cellulose ether may be the same as or different from the DS and if present, MS of the first water-soluble cellulose ether. This means that DS of the second water-soluble cellulose ether may be same or different from the DS of the first water-soluble cellulose ether, and when the first water-soluble cellulose ether contains hydroxypropoxy groups, MS of the second water-soluble cellulose ether may be same or different from the MS of the first water-soluble cellulose ether. The third water-soluble cellulose ether is selected from members in a Group different from the Group of the first water-soluble cellulose ether.

By using the first and the second water-soluble cellulose ethers which are the same members in the same Group, have different viscosities, and may have the same or different substitution degrees, the solubility of the film is improved, while maintaining the strength of the film. By adding a third water-soluble cellulose ether which is a member in the different Group from the Group of the first and second water-soluble cellulose ethers, the solubility of the film is further improved and the gelation characteristics (the thermal gelation temperature and the storage modulus G' at 80° C.) of the composition for forming a film can be enhanced.

Group 1 of the water-soluble cellulose ethers consists of two members providing excellent solubility.

More specifically, Group I consists of hydroxypropyl methyl cellulose Ia having a degree of substitution (DS) of methoxy groups of from 1.10 to 1.60, preferably from 1.30 to 1.60, and a molar substitution (MS) of hydroxypropoxy groups of from 0.10 to 0.33, preferably from 0.20 to 0.30; and hydroxypropyl methyl cellulose Ib having a degree of substitution (DS) of methoxy groups of from 1.80 to 2.00, preferably 1.85 to 2.00, and a molar substitution (MS) of hydroxypropoxy groups of from 0.20 to 0.34, preferably from 0.22 to 0.30.

Group II of the water-soluble cellulose ethers consists of two members providing excellent gelation properties.

More specifically, Group II consists of hydroxypropyl methyl cellulose IIa having a degree of substitution (DS) of the methoxy groups of from 1.70 to 2.00, preferably from 1.80 to 1.95, and a molar substitution (MS) of the hydroxypropoxy groups of from 0.10 to 0.18, preferably from 0.10 to 0.17; and methyl cellulose IIb having a degree of substitution (DS) of the methoxy groups of from 1.60 to 2.00, preferably from 1.75 to 1.95.

The combination of the members as the first, second and third water-soluble cellulose ethers, as this order of combination in parentheses, i.e., when expressed as "(member of the first water-soluble cellulose ether, member of the second water-soluble cellulose ether, member of the third water-soluble cellulose ether), includes (Ia, Ia, IIa), (Ia, Ia, IIb), (Ib, Ib, IIa), (Ib, Ib, IIb), (IIa, IIa, Ia), (IIa, IIa, Ib), (IIb, IIb, Ia), and (IIb, IIb, Ib)). The combination is preferably (Ia, Ia, IIa), (Ib, Ib, IIa), (IIa, IIa, Ia) or (IIa, IIa, Ib), and more preferably (Ib, Ib, IIa) or (IIa, IIa, Ib).

The second water-soluble cellulose ether is the same member as that of the first water-soluble cellulose ether, and the substitution degree or degrees of the second water-soluble cellulose ether may be the same as or different from the substitution degree or degrees of the first water-soluble cellulose ether, in other words, a degree of substitution (DS) of methoxy groups and if present, a molar substitution (MS) of hydroxypropoxy groups of the second water-soluble cellulose ether may be the same as or different from the DS and if present, MS of the first water-soluble cellulose ether. The second water-soluble cellulose ether having the same substitution degree or degrees as those of the first water-soluble cellulose ether can be obtained by adjusting to a desired viscosity different from that of the first water-soluble cellulose ether, for example, based on the difference in the degree of depolymerization. The second water-soluble cellulose ether is preferably the same member and has the same substitution degree or degrees as those of the first water-soluble cellulose ether from the viewpoint of easy adjustment of viscosity through depolymerization.

A degree of substitution (DS) of the methoxy groups and a molar substitution (MS) of the hydroxypropoxy groups with respect to hydroxypropyl methyl cellulose may be determined by converting the values measured in accordance with the assay for measuring the substitution degrees of "Hypromellose" and "Methyl cellulose" in the Japanese Pharmacopoeia Seventeenth Edition.

<Properties of Mixture Obtained by Blending Water-Soluble Cellulose Ethers>

The first, second and third water-soluble cellulose ethers are blended to obtain a mixture preferably having the following properties, so that a composition containing the mixture can have excellent gelation characteristics. The composition containing the mixture can form a film excellent in solubility and the like.

A degree of substitution (DS) of the methoxy groups of the water-soluble cellulose ether mixture obtained by blending the first, second and third water-soluble cellulose ethers is preferably from 1.50 to 2.00, more preferably from 1.6 to 2.00, and still more preferably from 1.70 to 1.95, from the viewpoint of gelation characteristics of the film-forming composition or solubility of the film.

A molar substitution (MS) of the hydroxypropoxy groups of the water-soluble cellulose ether mixture obtained by blending the first, second and third water-soluble cellulose ethers is preferably from 0.15 to 0.23, more preferably from 0.16 to 0.22, and still more preferably from 0.17 to 0.21, from the viewpoint of gelling characteristics of the film-forming composition or flexibility of the film.

A degree of substitution (DS) of the methoxy groups and a molar substitution (MS) of the hydroxypropoxy groups of the water-soluble cellulose ether mixture obtained by blending the first, second and third water-soluble cellulose ether may be determined by converting the values measured in accordance with the assay of measuring the substitution degrees of "Hypromellose" in the Japanese Pharmacopoeia Seventeenth Edition.

The viscosity at 20° C. of the 2% by mass aqueous solution of the water-soluble cellulose ether mixture obtained by blending the first, second and third water-soluble cellulose ethers is preferably from 3.0 to 15.0 mPa·s, more preferably from 4.0 to 12.0 mPa·s, and still more preferably from 4.5 to 10.0 mPa·s, from the viewpoint of strength or thickness control of the film.

Since the viscosity at 20° C. of the 2% by mass aqueous solution of the water-soluble cellulose ether mixture to be used in the composition for forming a film is less than 600 mPa·s after blending, the viscosity may be determined by using a Ubbelohde type viscometer in accordance with the viscosity measurement by capillary viscometer of the General Tests in the Japanese Pharmacopoeia Seventeenth Edition.

The thermal gelation temperature of a 20% by mass aqueous solution of water-soluble cellulose ether mixture obtained by blending the first, second and third water-soluble cellulose ethers is preferably from 38 to 60° C., more preferably from 40 to 58° C., and still more preferably from 42 to 56° C., from the viewpoint of film thickness control.

The storage modulus G' at 80° C. of a 20% by mass aqueous solution of the water-soluble cellulose ether mixture obtained by blending the first, second and third water-soluble cellulose ethers is preferably from 20,000 to 150,000 Pa, more preferably from 21,000 to 100,000 Pa, still more preferably from 22,000 to 75,000 Pa, and particularly preferably from 23,000 to 50,000 Pa, from the viewpoint of forming a film having a uniform film thickness on a three-dimensional substrate such as a capsule-mold pin.

The thermal gelation temperature and the storage modulus G' at 80° C. of a 20% by mass aqueous solution of water-soluble cellulose ether mixture to be used in the composition for forming a film may be determined, for example, by a MCR301 which is a rheometer manufactured by Anton Paar.

The temperature of a sample measurement section of the rheometer is adjusted to 20° C. in advance, and a 20% by mass aqueous solution of water-soluble cellulose ether mixture to be used for the film-forming composition is set in the sample measurement section, Parallel plates (PP-50) having a diameter of 50 mm are used as a measurement jig. The measurement gap is set to 0.5 mm, and then an excess of the solutions is removed. In order to prevent evaporation of a solvent, an outer periphery of the measurement jig is covered with a silicone oil, and the solution is then left stand at 20° C. for 5 minutes. Thereafter, the measurement is started by applying a distortion at a frequency of 1 Hz and an amplitude of 1%. The temperature of the sample measurement section is increased from 20 to 90° C. at a rate of 2° C./min by using Peltier temperature control, while collecting data at two points per minute. The storage modulus G' (20→90° C.) obtained in this measurement generally indicates an elastic property of the solution, and the loss elastic modulus G" (20→90° C.) generally indicates a viscous property of the solution. In other words, when a measurement sample is in the liquid state, G">G' is satisfied, and when it is in the gel (solid) state, G"<G' is satisfied. The temperature at the time of satisfying G"=G' is designated as the thermal gelation temperature.

<Content of Each Water-Soluble Cellulose Ether>

When the first, second and third water-soluble cellulose ethers are blended to obtain a mixture having the above-described properties, a preferred content of each water-soluble cellulose ether in the composition for forming a film will be described. The first, second and third water-soluble cellulose ethers may be blended in advance and then mixed with the other component or components in the composition for forming a film. Alternatively, the other component or components may be mixed together with one or more of the water-soluble cellulose ethers.

The content of the first water-soluble cellulose ether in the composition for forming a film is preferably from 3.0 to 15.0% by mass, more preferably from 3.0 to 13.0% by mass, from the viewpoint of strength or solubility of the film.

The content of the second water-soluble cellulose ether in the composition for forming a film is preferably from 0.5 to 7.0% by mass, more preferably from 0.8 to 6.0% by mass, from the viewpoint of the strength or the thickness control of the film.

The content of the third water-soluble cellulose ether in the composition for forming a film is preferably from 4.0 to 18.0% by mass, more preferably from 5.0 to 15.0% by mass, from the viewpoint of solubility or gelling characteristics of the film.

<Flow to Obtain Each Water-Soluble Cellulose Ether>

The first, second and third water-soluble cellulose ethers may be purchased as commercial products, or may be produced by a known method such as the method described below.

A water-soluble cellulose ether may be produced by a method comprising steps of: bringing cellulose pulp into contact with an alkali metal hydroxide solution such as an aqueous sodium hydroxide solution to obtain alkali cellulose, reacting the alkali cellulose with an etherifying agent such as methyl chloride or propylene oxide at 60 to 100° C. to obtain a reaction product, and washing, drying and pulverizing the reaction product. The method for producing a water-soluble cellulose ether may comprise, thereafter, an optional step of depolymerizing the obtained water-soluble cellulose ether, for example, in the presence of an acid (e.g. hydrochloric acid) at 50 to 95° C. for 20 to 120 minutes for reduction of the viscosity to obtain a water-soluble cellulose ether having a desired substitution degree or degrees and a desired viscosity.

(2) Solvent

Next, a solvent to be used in the composition for forming a film will be described.

The solvent is not particularly limited as long as the solvent can completely dissolve the water-soluble cellulose ethers. Examples of the solvent include water and a mixed solvent of water and a lower alcohol having 1 to 4 carbon atoms. A commercially available solvent may be used as the solvent. The solvent may be used in combination of two or more types, if necessary. As a solvent to be used in the composition for forming a film, water is preferred from the viewpoint of safety and environmental aspects.

Examples of the lower alcohol having 1 to 4 carbon atoms include methanol, ethanol, and propanol. The content of water in the mixed solvent is not particularly limited. It is preferably from 20.0 to 99.9% by mass in the total mass of the mixed solvent from the viewpoint of maintaining uniformity of the composition for forming a film.

The content of the solvent to be used in the composition for forming a film is preferably from 60.0 to 92.5% by mass, more preferably from 70.0 to 88.0% by mass, from the viewpoint of controlling the film thickness.

(3) Additive

The composition for forming a film may optionally comprise an additive such as a gelling agent, a gelling aid, a plasticizer, a pigment, and a flavoring agent. However, the composition for forming a film preferably contains no water-soluble cellulose ether other than the first, second and third water-soluble cellulose ethers described above. The additive is preferably added in such a manner that the additive is uniformly dissolved or dispersed in the composition for forming a film. The additive may be used in combination of two or more, if necessary. A commercial additive may be used.

The gelling agent is not particularly limited as long as the film-forming composition can gel around room temperature (i.e., at from 15 to 35° C.). Examples of the gelling agent may include kappa carrageenan (k-carrageenan), iota carrageenan (i-carrageenan), gellan gum, pectin, curdlan, agar, and tamarind gum.

When a gelling agent is used, an amount of the gelling agent in the composition for forming a film is preferably from 0.50 to 5.0 parts by mass, more preferably from 0.75 to 3.0 parts by mass, relative to 100 parts by mass of the water-soluble cellulose ether mixture to be used in the composition for forming a film, from the viewpoint of solubility or thickness control of the film.

The film-forming composition containing the first, second and third water-soluble cellulose ethers can sufficiently form a film by heating due to their thermal gelation characteristics, so that the film-forming composition preferably contains no gelling agent.

Examples of the gelling aid include potassium chloride, calcium chloride, ammonium chloride, and ammonium acetate.

An amount of the gelling aid in the composition for forming a film is preferably 10.0 parts by mass or less, more preferably from 0.25 to 2.0 parts by mass, relative to 100 parts by mass of the water-soluble cellulose ether mixture to be used in the composition for forming a film, from the viewpoint of preventing precipitation of the gelling aid.

The plasticizer is not particularly limited as long as it is usable in a pharmaceutical or a food. Examples of the plasticizer include triethyl citrate, triacetin, polysorbate 80 (Tween® 80), polyethylene glycol, and dioctyl sodium sulfosuccinate.

An amount of the plasticizer in the composition for forming a film is preferably 30.0 parts by mass or less, more preferably from 0.1 to 15.0 parts by mass, relative to 100 parts by mass of the water-soluble cellulose ether mixture to be used in the composition for forming a film, from the viewpoint of strength of the film.

Examples of the pigment include titanium oxide, an aluminum lake, and an edible dye.

An amount of the pigment in the composition for forming a film varies depending on the purpose of addition such as light shielding and coloring. It is preferably 5.0 parts by mass or less, more preferably from 0.1 to 2.5 parts by mass, relative to 100 parts by mass of the water-soluble cellulose ether mixture to be used in the composition for forming a film, from the viewpoint of the strength of the film.

Examples of the flavoring agent include essential oils such as lemon oil, orange oil, peppermint, spearmint, and hacka; and synthetic flavors such as coffee flavor and yogurt flavor.

An amount of the flavoring agent in the composition for forming a film is preferably 2.5 parts by mass or less, more preferably from 0.1 to 1.0 parts by mass, relative to 100 parts by mass of the water-soluble cellulose ether mixture to be used in the composition for forming a film, from the viewpoint of the strength of the film.

2. Method for Producing Composition for Forming Film

The composition for forming a film may be produced by, for example, the following method.

A first method for producing a composition for forming a film in the absence of a gelling agent comprises steps of: mixing the first, second and third water-soluble cellulose ethers, a solvent of preferably 85° C. or higher, more preferably from 90 to 98° C., and an optional additive excluding a gelling agent with stirring at 300 to 1000 rpm for 5 to 15 minutes in a hot water bath of 80 to 95° C., while placing a cover for preventing the solvent from evaporating, so as to sufficiently disperse the water-soluble cellulose ethers in the solvent; cooling the resulting mixture in a water bath of 5 to 10° C. with stirring at 50 to 100 ppm for 1.5 to 3 hours so as to completely dissolve the water-soluble cellulose ethers; removing the cooled mixture from the water bath; and then leaving the cooled mixture stand preferably at 5 to 10° C. for 1 to 2 days and further at 20 to 25° C. for 1 to 2 days for defoaming.

A second method for producing a composition for forming a film in the presence of a gelling agent comprises steps of: mixing the first, second third water-soluble cellulose ethers, a solvent of preferably from 85 to 98° C., and a gelling agent as an additive to obtain a dispersion in which the water-soluble cellulose ethers are sufficiently dispersed in the solvent; and defoaming the obtained dispersion at a temperature of preferably 80° C. or higher to obtain a slurry-like film-forming composition in which the water-soluble cellulose ethers are dispersed in the solvent.

Further, the film-forming composition produced in the first method in the absence of a gelling agent is warmed to a dissolution temperature or higher of a gelling agent, and is subjected to addition of the gelling agent to completely dissolve the gelling agent. As a result, there can be also produced a film-forming composition in which the water-soluble cellulose ethers are uniformly dissolved.

3. Applications of Composition for Forming Film

The film-forming composition can produce a film in a film-forming method, so that it is applicable for a film preparation, a hard capsule preparation, a film-coated preparation, and the like. It is preferably suitable for a hard capsule requiring high strength because the strength of the film is not greatly impaired.

The film may be produced by applying the film-forming composition on a base such as a glass plate using a bar coater or an applicator, or by immersing a base such as a capsule mold pin in the film-forming composition and taking the base out of the composition; and then removing a solvent from the composition on the base. In other words, the film may be produced by a method comprising steps of: applying the film-forming composition on a base, removing a solvent from the composition on the base to obtain a film, and optionally detaching the film from the base.

Further, the film may be produced by a method comprising a step of spraying the film-forming composition onto a tablet or the like, while evaporating a solvent from the composition.

When a film-forming composition not containing a gelling agent is used as a film preparation, for example, 30 to 50 g of the film-forming composition of 5 to 30° C. is poured onto a glass plate of 40 to 95° C. kept horizontal so as not to form air bubbles, and is subjected to casting with a YBA type baker-applicator (produced by Yoshimitsu Seiki Co., Ltd.). Then, the composition on the glass plate is dried or subjected to solvent removal, while keeping the glass plate horizontal, for example, in a windless dryer having an inside temperature of 40 to 95° C. to form a film. It is dried or solvent-removed until the water content or solvent content of the film becomes 5% by mass or less, and then the film is detached from the glass plate.

When a film-forming composition containing a gelling agent is used as a film preparation, a film may be obtained by flow-casting the film-forming composition having a temperature equal to or higher than the gelation temperature of the gelling agent, on a glass plate having a temperature equal to or lower than the gelation temperature of the gelling agent, and drying or solvent-removing the composition at a temperature equal to or lower than the gelation temperature of the gelling agent.

The hard capsule may be produced by immersing a capsule mold pin in the film-forming composition, taking the pin out of the composition, drying or solvent-removing the composition adhering to the pin to form a film on the pin, then detaching the film from the pin, and cutting and fitting the film.

Examples of a method for producing a hard capsule include, but not limited to, a cold pin method and a hot pin method. In the cold pin method, for example, a pin of 5 to 20° C. is immersed in the film-forming composition containing a gelling agent. In the hot pin method, for example, a pin of 40 to 95° C. is immersed in the film-forming composition containing no gelling agent.

The film-coated preparation may be produced, for example, by applying the film-forming composition to a tablet, a granule, a fine granule or a core particle, while drying or solvent-removing the composition, by using a coating apparatus such as a pan coating apparatus, a fluidized bed coating apparatus and a tumbling fluidized bed coating apparatus.

EXAMPLES

Hereinafter, the invention will be described more specifically with reference to Examples and Comparative Examples. However, it should not be construed that the invention is limited to or by Examples.

<Syntheses of HPMCs>

Chips of wood pulp were immersed in a 49% by mass aqueous sodium hydroxide solution, and an excess aqueous sodium hydroxide solution was removed to obtain alkali cellulose having a mass ratio of alkali metal hydroxide to a solid component in the pulp of 030. The 18.8 kg of this alkaline cellulose was placed in a pressure-resistant reactor, and after vacuuming, 9 kg of methyl chloride and 3.1 kg of propylene oxide were added thereto for the reaction. After the reaction was over, the product mixture was washed, dried, and pulverized to obtain HPMC.

The HPMC was subjected to spraying of hydrochloric acid and then transferred into a 2 L glass reactor. While rotating the glass reactor with heating in a water bath of 85° C., depolymerization reaction was carried out for 90 minutes to obtain HPMC-Ia-1 having a degree of substitution (DS) of the methoxy groups of 1.46, a molar substitution (MS) of the hydroxypropoxy groups of 0.25, and a viscosity at 20° C. of 3.5 mPa·s, as determined in a 2% by mass aqueous solution.

Various types of HPMC-Ia, HPMC-Ib and HPMC-IIa were synthesized in the same manner as HPMC-Ia-1.

A viscosity at 20° C. of the 2% by mass of an aqueous solution, a degree of substitution (DS) of the methoxy groups, and a molar substitution (MS) of the hydroxypropoxy groups with respect to each synthesized HPMC are shown in Tables 1 and 2

<Syntheses of MCs>

Chips of wood pulp were immersed in a 49% by mass aqueous sodium hydroxide solution, and an excess aqueous sodium hydroxide solution was removed to obtain alkali cellulose having a mass ratio of alkali metal hydroxide to a solid component in the pulp of 1.00. The 17.2 kg of this alkali cellulose was placed into a pressure-resistant reactor, and after vacuuming, 9 kg of methyl chloride was added thereto for the reaction. After the reaction was over, the product mixture was washed, dried, and pulverized to obtain MC.

The depolymerization reaction was carried out in the same manner as in the depolymerization reaction of HPMC to obtain MC-IIb-1 having a degree of substitution (DS) of the methoxy groups of 1.77, and a viscosity at 20° C. of 2.9 mPa's, as determined in a 2% by mass aqueous solution.

Various types of MC-IIb were synthesized in the same manner as in MC-IIb-1.

A viscosity at 20° C. of a 2% by mass aqueous solution, and a degree of substitution (DS) of the methoxy groups with respect to each synthesized MC are shown in Table 2.

TABLE 1 water-soluble cellulose ether in Group I

| type | No. | viscosity (mPa · s) | DS (-) | MS (-) |
|---|---|---|---|---|
| HPMC-Ia | 1 | 3.5 | 1.46 | 0.25 |
| | 2 | 4.6 | 1.46 | 0.25 |
| | 3 | 6.4 | 1.46 | 0.25 |
| | 4 | 8.0 | 1.46 | 0.25 |
| | 5 | 11.8 | 1.46 | 0.25 |
| | 6 | 15.0 | 1.46 | 0.25 |
| HPMC-Ib | 1 | 3.0 | 1.90 | 0.25 |
| | 2 | 4.5 | 1.88 | 0.24 |
| | 3 | 6.0 | 1.88 | 0.24 |
| | 4 | 9.2 | 1.90 | 0.25 |
| | 5 | 7.7 | 1.90 | 0.25 |
| | 6 | 11.5 | 1.90 | 0.25 |
| | 7 | 48.0 | 1.90 | 0.25 |

TABLE 2 water-soluble cellulose ether in Group II

| type | No. | viscosity (mPa · s) | DS (-) | MS (-) |
|---|---|---|---|---|
| HPMC-IIa | 1 | 3.3 | 1.88 | 0.16 |
| | 2 | 4.5 | 1.88 | 0.16 |
| | 3 | 4.9 | 1.88 | 0.16 |
| | 4 | 6.1 | 1.88 | 0.16 |
| | 5 | 17.0 | 1.88 | 0.16 |
| | 6 | 32.6 | 1.88 | 0.16 |
| MC-IIb | 1 | 2.9 | 1.77 | — |
| | 2 | 4.0 | 1.77 | — |
| | 3 | 20.3 | 1.77 | — |

Example 1

The 8 g of HPMC-Ib-1, 12 g of HPMC-Ib-4 and 20 g of HPMC-IIa-4 were placed in 300 mL of glass beaker, and then hot water of 90° C. was added thereto to make a total mass of 200 g. The resulting mixture was stirred at 500 rpm in a hot water bath of 80° C. for 10 minutes after putting a cover thereon for preventing evaporation of the solvent. After confirming that HPMCs were sufficiently dispersed in the hot water, the beaker was placed in a water bath of 5° C., and then the mixture in the beaker was stirred at 50 rpm for another 2 hours to completely dissolve HPMCs. The beaker was taken out of the water bath, and left stand at 6° C. for 1 day and further at 20° C. for 1 day for defoaming in a sealed state so as to prevent evaporation of the solvent.

<Viscosity Measurement of Mixture of Water-soluble Cellulose Ethers>

The 10.0 of the film-forming composition produced by the above method was mixed with 90.0 g of pure water in a 200-mL glass beaker to prepare a 2% by mass aqueous solution of the water-soluble cellulose ethers. Thereafter, the viscosity at 20° C. of the 2% by mass aqueous solution of the water-soluble cellulose ethers contained in the film-forming composition was measured using a Ubbelohde type viscometer in accordance with the viscosity measurement by capillary viscometer of the General Tests in the Japanese Pharmacopoeia Seventeenth Edition.

<Measurement of Thermal Gelation Temperature and Storage Modulus G' of Mixture of Water-Soluble Cellulose Ethers>

The thermal gelation temperature and the storage modulus G' at 80° C. of the water-soluble cellulose ether mixture were measured by using IVICR301 which was a rheometer produced by Anton Paar. The results are shown in Table 3.

<Preparation of Film>

Approximately 40 g of the film-forming composition having a temperature of 20° C. was poured on a glass plate of 60° C. which was kept horizontal in such a manner as not to cause air bubbles to enter, and the composition was flow-cast manually on the glass plate by using a YBA type baker applicator (produced by Yoshimitsu Seiki Co., Ltd.). Then, the glass plate was placed, while kept horizontal, in a windless dryer, and dried at 60° C. until the water content of the film formed on the glass plate became 5% by mass or less. Then, the film was detached from the glass plate to obtain a film having a thickness of 100±5 µm.

<Measurement of Film Strength>

The obtained film was cut into strips of 8 cm in length and 1 cm in width, dried at 80° C. for 2 hours, and then subjected to humidity control in an environment of 25° C. and 52 RH % for 3 days to prepare film test pieces having a moisture content of 6.5±0.5% by mass, as determined by a heating type moisture meter (MX-50 produced by A&D Company Limited).

Tensile test was carried out in a constant temperature and constant humidity machine (PR-33 produced by ESPEC Corporation, PR-33 having two φ15 cm operation ports on the front door) which was set to 25° C. and 52 RH %, by using a tabletop small tensile tester (MODEL-FTN-1-13A produced by Aikoh Engineering Co., Ltd.). To prevent slipping of the film, the test piece was fixed at the positions of 2 cm inside from the top and 2 cm inside from the bottom of the test piece by jigs having a soft vinyl chloride sheet attached to flat chuck (MODEL-023 produced by Aikoh Engineering Co., Ltd.). The measurement was made under conditions of a fulcrum distance of 4 cm, a test velocity of 1.0 mm/min and a load cell rating of 500 N. The average value of the film strength. (n=10) was calculated. The film strength obtained in the measurement is shown in Table 3.

<Measurement of Dissolution Time of Film>

For the evaluation of the solubility, a sample holder to be used was prepared based on the auxiliary tube described in the Disintegration Test of the Japanese Pharmacopoeia Seventeenth Edition, while referring to JP 2015-522614A, which was Japanese phase publication of WO 2014/018279 A1. The sample holder comprises a first sample holder body part 1, a first chrome steel ball. 2, a sample holder lid 3, a silicone rubber packing 4, a second sample holder body part 6, and a second chrome steel ball. 7.

The first sample holder body part 1 is a body part (inner diameter 12 mm, outer diameter 17 mm and length of 20 mm) of the auxiliary tube to be used in the Disintegration Test, and the sample holder lid 3 is obtained by removing a wire mesh from a lid (inner diameter of 2 mm, outer diameter of 17 mm and length of 4 mm) of the auxiliary tube to be used in the Disintegration Test. The second sample holder body part 6 is formed by combining a body part of the auxiliary tube to be used in the Disintegration Test with a lid (inner diameter of 12 mm, outer diameter of 17 mm and length of 4 mm) of the auxiliary tube, wherein a hole in the side surface of the body part of the auxiliary tube is completely closed with a silicone rubber, and a wire mesh of the lid of the auxiliary tube is completely closed with a silicone rubber. The silicone rubber packing 4 having an inner diameter of 10 mm, an outer diameter of 14 mm and a thickness of 0.5 mm was used fir the purpose of fixing the film and keeping an area of the film to be contacted with water constant during the test. The first chrome steel ball 2 having a weight of about 1.0 g and a diameter of about 6.35 mm (¼ inches) was used for the purpose of reproducing the stress on the HPMC film in the stomach. The second chrome steel ball 7 having a weight of about 3.55 g and a diameter of about 9.53 mm (⅜ inches) was used for the purpose of preventing the second sample holder from floating during the test.

The dissolution time of the films was measured as follows: First, the obtained film was dried at 80° C. for 2 hours, and then subjected to humidity control in an environment of 25° C. and 52 RH % for 3 days to have a water content of 6.5±0.5% by mass, as determined by a heating type moisture meter (MX-50 produced by A&D Company Limited). Thereafter, the film piece 5 having φ14 mm, obtained by punching the film, was placed between the second sample holder body part 6 containing the second chrome steel ball 7 and the silicone rubber packing 4, while keeping the surface exposed to air during the formation of film upward. Then, the film piece 5 was further fixed by the sample holder lid 3 from above.

Next, the first sample holder body part 1 and the sample holder lid 3 were fixed without a gap by an adhesive tape, the first chrome steel ball 2 was placed on the film, and the sample holder was set in the basket-rack assembly described in the Disintegration Test of the Japanese Pharmacopoeia Seventeenth Edition. And 1150 mL of pure water was placed in a low-sized beaker, the basket-rack assembly was placed in the low-sized beaker, and the dissolution time of the film was measured (n=6) by using a disintegration tester (NT-400 produced by Toyama Sangyo Co., Ltd.) under the conditions of a water temperature of 37±0.5° C. and raising and lowering the basket between the distance of 55 mm at a reciprocation rate of 15 cycles (reciprocations) per minute. The dissolution time of the film is defined as the elapsed time from the start of the test until the first chrome steel ball 2 enters into the second sample holder body part 6 through the film and contacts with the second chrome steel ball 7. The dissolution time of the film obtained by measurement is shown in Table 3.

Considering that the film dissolves in the stomach, it is appropriate to perform the test using the first solution having pH a value of 1.2 of the Disintegration Test. However, since the solubility of HPMC film is almost equivalent between in pure water and in the first solution of the Disintegration Test, the film was evaluated using pure water.

Examples 2 to 11 and Comparative Examples 1 to 6

A composition for forming a film was produced by the same method as in Example 1 except that the formation was changed to one of those shown in Tables 3 and 4. The produced composition was evaluated with respect to various properties in the same manner as in Example 1. Further, a film was prepared in the same manner as in Example 1, and subjected to measurements of the strength and dissolution time. The results are shown in Tables 3 and 4.

TABLE 3

| | Composition for forming a film | | | | | | | | | | | | |
|---|---|---|---|---|---|---|---|---|---|---|---|---|---|
| | water-soluble cellulose ether | | | | | | mixture of water-soluble cellulose ethers | | | | | film | |
| | first (% by mass) | second (% by mass) | third (% by mass) | others (% by mass) | difference in viscosity between 1st and 2nd (mPa·s) | solvent (% by mass) | DS (—) | MS (—) | viscosity (mPa·s) | thermal gelation temperature (° C.) | storage modulus G' at 80° C. (Pa) | strength (N/mm²) | dissolution time (min) |
| Example 1 | HPMC-Ib-1 (4.0) | HPMC-Ib-4 (6.0) | HPMC-IIa-4 (10.0) | — | 6.2 | water (80.0) | 1.89 | 0.20 | 6.1 | 55 | 26210 | 61.9 | 8.6 |
| Example 2 | HPMC-Ib-1 (7.8) | HPMC-Ib-7 (2.2) | HPMC-IIa-4 (10.0) | — | 45.0 | water (80.0) | 1.89 | 0.20 | 5.1 | 54 | 27830 | 59.4 | 9.1 |
| Example 3 | HPMC-Ib-2 (6.0) | HPMC-Ib-5 (5.0) | HPMC-IIa-4 (10.0) | — | 3.2 | water (80.0) | 1.89 | 0.20 | 6.0 | 54 | 26990 | 62.7 | 8.4 |
| Example 4 | HPMC-IIa-1 (4.5) | HPMC-IIa-4 (5.5) | HPMC-Ib-2 (10.0) | — | 2.8 | water (80.0) | 1.89 | 0.20 | 4.6 | 53 | 25970 | 57.9 | 7.4 |
| Example 5 | HPMC-IIa-1 (7.7) | HPMC-IIa-5 (2.3) | HPMC-Ib-2 (10.0) | — | 13.7 | water (80.0) | 1.89 | 0.20 | 4.6 | 53 | 25500 | 57.2 | 7.3 |
| Example 6 | HPMC-IIa-1 (11.3) | HPMC-IIa-5 (3.7) | HPMC-Ia-6 (5.0) | — | 13.7 | water (80.0) | 1.78 | 0.18 | 6.8 | 52 | 24000 | 59.5 | 10.1 |
| Example 7 | HPMC-IIa-1 (12.8) | HPMC-IIa-5 (2.2) | HPMC-Ia-5 (5.0) | — | 29.3 | water (80.0) | 1.78 | 0.18 | 6.8 | 52 | 23100 | 61.3 | 9.7 |
| Example 8 | HPMC-Ia-1 (3.0) | HPMC-Ia-3 (2.0) | HPMC-IIa-4 (15.0) | — | 2.9 | water (80.0) | 1.78 | 0.18 | 5.5 | 53 | 26950 | 60.4 | 9.3 |
| Example 9 | HPMC-Ia-1 (4.0) | HPMC-Ia-5 (1.0) | HPMC-IIa-4 (15.0) | — | 8.3 | water (80.0) | 1.78 | 0.18 | 5.5 | 53 | 23930 | 58.4 | 6.4 |
| Example 10 | MC-IIb-1 (6.8) | MC-IIb-3 (1.2) | HPMC-Ib-5 (12.0) | — | 17.4 | water (80.0) | 1.85 | 0.15 | 7.9 | 46 | 49240 | 55.0 | 10.8 |
| Example 11 | MC-IIb-1 (5.2) | MC-IIb-3 (0.8) | HPMC-Ia-4 (14.0) | — | 17.4 | water (80.0) | 1.56 | 0.18 | 6.6 | 43 | 20120 | 56.5 | 8.2 |

TABLE 4

| | Composition for forming a film | | | | | | | | | | | |
|---|---|---|---|---|---|---|---|---|---|---|---|---|
| | water-soluble cellulose ether | | | | | mixture of water-soluble cellulose ethers | | | | | | |
| | | | | | difference | | | | | thermal | storage | film |
| | | | | | in viscosity | | | | | gelation | modulus | | dissolution |
| | | | | others | between | solvent | | | | temperature | G' at | strength | lution |
| | first | second | third | (% by | 1st and 2nd | (% by | DS | MS | viscosity | 80° C. | | time |
| | (% by mass) | (% by mass) | (% by mass) | mass) | (mPa·s) | mass) | (—) | (—) | (mPa·s) | (° C.) | (Pa) | (N/mm²) | (min) |
| Comp. Ex. 1 | none | HPMC-Ib-3 (10.0) | HPMC-IIa-4 (10.0) | — | — | water (80.0) | 1.89 | 0.20 | 6.0 | 55 | 29060 | 61.0 | 9.9 |
| Comp. Ex. 2 | HPMC-IIa-2 (10.0) | none | HPMC-Ib-2 (10.0) | — | — | water (80.0) | 1.89 | 0.20 | 4.5 | 54 | 24900 | 58.4 | 7.8 |
| Comp. Ex. 3 | none | none | HPMC-IIa-3 (15.0) | HPMC-Ia-6 (5.0) | — | water (80.0) | 1.78 | 0.18 | 6.8 | 53 | 24850 | 57.1 | 10.7 |
| Comp. Ex. 4 | none | none | HPMC-Ia-2 (5.0) | HPMC-IIa-4 (15.0) | — | water (80.0) | 1.78 | 0.18 | 5.4 | 53 | 25620 | 57.5 | 9.8 |
| Comp. Ex. 5 | MC-IIb-2 (8.0) | none | HPMC-Ib-5 (12.0) | — | — | water (80.0) | 1.84 | 0.15 | 7.8 | 46 | 50500 | 58.2 | 11.8 |
| Comp. Ex. 6 | MC-IIb-2 (6.0) | none | HPMC-Ia-4 (14.0) | — | — | water (80.0) | 1.56 | 0.18 | 6.6 | 42 | 19400 | 55.8 | 10.2 |

In general, when the viscosity of the water-soluble cellulose ether becomes lower, or when a molar substitution (MS) of the hydroxypropoxy groups of the water-soluble cellulose ether becomes higher with the proviso of maintaining the same viscosity, the solubility of the water-soluble cellulose ether becomes higher. Accordingly, the comparison and discussion should be made between Examples and Comparative Examples in which the viscosity and the substitution degrees of the mixture of the water-soluble cellulose ethers contained in the composition for forming a film are almost the same.

The results of each of Examples 1 to 3 show the film strength of 59.0 N/mm² or higher, and the dissolution time shortened by 0.8 to 1.5 minutes compared with that in Comparative Example 1.

The results of each of Examples 4 and 5 show the film strength of 57.0 N/mm² or higher, and the dissolution time shortened by 0.4 to 0.5 minutes compared with that in Comparative Example 2.

The results of each of Examples 6 and 7 show the film strength of 59.0 N/mm² or higher, and the dissolution time shortened by 0.6 to 1.0 minutes compared with that in Comparative Example 3.

The results of each of Examples 8 and 9 show the film strength of 58.0 N/mm² or higher and the dissolution time shortened by 0.5 to 1.4 minutes compared with that in Comparative Example 4.

The results of Example 10 show the film strength of 55.0 N/mm² and the dissolution time shortened by 1.0 minute compared with that in Comparative Example 5.

The results of Example 11 show the film strength of 56.5 N/mm² and the dissolution time shortened by 2.0 minutes compared with that in Comparative Example 6.

As described above, it has been found that by combining the same members of the first and second water-soluble cellulose ethers having the different viscosity values and the same or different substitution degree or degrees, with the different member of the third water-soluble cellulose ether selected from a Group different from the Group of the first and second water-soluble cellulose ethers, a film excellent in strength and solubility can be formed. It is considered to be because by incorporation of the second water-soluble cellulose ether having high viscosity, entanglement of the water-soluble cellulose ethers in the film is maintained so that the film strength is maintained in Examples. Further, it is considered to be because by incorporation of the first water-soluble cellulose ether having a low viscosity, the first water-soluble cellulose ether is preferentially eluded during the solubility test so that the dissolution in Examples can exhibit better solubility than that in Comparative Examples. Further, it is considered to be because by incorporation of the third water-soluble cellulose ether, the preferable gelation characteristics may be maintained

The invention claimed is:

1. A composition for forming a film, the composition comprising:
   a first water-soluble cellulose ether having a viscosity at 20° C. of from 2.5 to 4.5 mPa·s, as determined in a 2% by mass aqueous solution;
   a second water-soluble cellulose ether having a viscosity at 20° C. of from 6.0 to 50.0 mPa·s, as determined in a 2% by mass aqueous solution;
   a third water-soluble cellulose ether having a viscosity at 20° C. of from 4.5 to 15.0 mPa·s, as determined in a 2% by mass aqueous solution; and
   a solvent;
wherein the first water-soluble cellulose ether is selected from four members:
   two members in Group I:
      hydroxypropyl methyl cellulose Ia having a degree of substitution (DS) of methoxy groups of from 1.10 to 1.60 and a molar substitution (MS) of hydroxypropoxy groups of from 0.10 to 0.33, and
      hydroxypropyl methyl cellulose Ib having a degree of substitution (DS) of methoxy groups of from 1.80 to 2.00 and a molar substitution (MS) of hydroxypropoxy groups of from 0.20 to 0.34, and
   two members both in Group II:
      hydroxypropyl methyl cellulose IIa having a degree of substitution (DS) of methoxy groups of from 1.70 to 2.00 and a molar substitution (MS) of hydroxypropoxy groups of from 0.10 to 0.18, and
      methyl cellulose IIb having a degree of substitution (DS) of methoxy groups of from 1.60 to 2.00,
wherein the second water-soluble cellulose ether is the same member as that of the first water-soluble cellulose ether, provided that DS and, if present, MS of the second water-soluble cellulose ether may be the same as or different from the DS and, if present, MS of the first water-soluble cellulose ether, and wherein the third water-soluble cellulose ether is selected from members in a Group different from the Group of the first water-soluble cellulose ether.

2. The composition for forming a film according to claim 1, wherein each of the first and second water-soluble cellulose ethers is the hydroxypropyl methyl cellulose IIa and the third water-soluble cellulose ether is the hydroxypropylmethylcellulose Ia or Ib.

3. The composition for forming a film according to claim 1, wherein each of the first and second water-soluble cellulose ethers is the hydroxypropyl methyl cellulose Ia or Ib, and the third water-soluble cellulose ether is the hydroxypropyl methyl cellulose IIa.

4. The composition for forming a film according to claim 1, wherein each of the first and second water-soluble cellulose ethers is the methyl cellulose IIb, and the third water-soluble cellulose ether is the hydroxypropyl methyl cellulose Ia or Ib.

5. The composition for forming a film according to claim 1, wherein a mixture obtained of the first, second and third water-soluble cellulose ethers has a degree of substitution (DS) of the methoxy groups of from 1.50 to 2.00, and a molar substitution (MS) of the hydroxypropoxy groups of from 0.15 to 0.22.

6. The composition for forming a film according to claim 1, wherein a mixture of the first, second and third water-soluble cellulose ethers has a viscosity at 20° C. of from 3.0 to 15.0 mPa·s, as determined in a 2% by mass aqueous solution.

7. The composition for forming a film according to claim 1, wherein a mixture of the first, second and third water-soluble cellulose ethers has a gelling temperature of from 38 to 60° C., as determined in a 20% by mass aqueous solution.

8. A film comprising:
a first water-soluble cellulose ether having a viscosity at 20° C. of from 2.5 to 4.5 mPa·s, as determined in a 2% by mass aqueous solution;
a second water-soluble cellulose ether having a viscosity at 20° C. of from 6.0 to 50.0 mPa·s, as determined in a 2% by mass aqueous solution; and
a third water-soluble cellulose ether having a viscosity at 20° C. of from 4.5 to 15.0 mPa·s, as determined in a 2% by mass aqueous solution;
wherein the first water-soluble cellulose ether is selected from four members:
two members in Group I:
hydroxypropyl methyl cellulose Ia having a degree of substitution (DS) of methoxy groups of from 1.10 to 1.60 and a molar substitution (MS) of hydroxypropoxy groups of from 0.10 to 0.33, and
hydroxypropyl methyl cellulose Ib having a degree of substitution (DS) of methoxy groups of from 1.80 to 2.00 and a molar substitution (MS) of hydroxypropoxy groups of from 0.20 to 0.34, and
two members both in Group II:
hydroxypropyl methyl cellulose IIa having a degree of substitution (DS) of methoxy groups of from 1.70 to 2.00 and a molar substitution (MS) of hydroxypropoxy groups of from 0.10 to 0.18, and
methyl cellulose IIb having a degree of substitution (DS) of methoxy groups of from 1.60 to 2.00,
wherein the second water-soluble cellulose ether is the same member as that of the first water-soluble cellulose ether, provided that DS and, if present, MS of the second water-soluble cellulose ether may be the same as or different from the DS and, if present, MS of the first water-soluble cellulose ether, and wherein the third water-soluble cellulose ether is selected from members in a Group different from the Group of the first water-soluble cellulose ether.

9. The composition for forming a film according to claim 2, wherein a mixture obtained of the first, second and third water-soluble cellulose ethers has a degree of substitution (DS) of the methoxy groups of from 1.50 to 2.00, and a molar substitution (MS) of the hydroxypropoxy groups of from 0.15 to 0.22.

10. The composition for forming a film according to claim 2, wherein a mixture of the first, second and third water-soluble cellulose ethers has a viscosity at 20° C. of from 3.0 to 15.0 mPa·s, as determined in a 2% by mass aqueous solution.

11. The composition for forming a film according to claim 2, wherein a mixture of the first, second and third water-soluble cellulose ethers has a gelling temperature of from 38 to 60° C., as determined in a 20% by mass aqueous solution.

12. The composition for forming a film according to claim 3, wherein a mixture obtained of the first, second and third water-soluble cellulose ethers has a degree of substitution (DS) of the methoxy groups of from 1.50 to 2.00, and a molar substitution (MS) of the hydroxypropoxy groups of from 0.15 to 0.22.

13. The composition for forming a film according to claim 3, wherein a mixture of the first, second and third water-soluble cellulose ethers has a viscosity at 20° C. of from 3.0 to 15.0 mPa·s, as determined in a 2% by mass aqueous solution.

14. The composition for forming a film according to claim 3, wherein a mixture of the first, second and third water-soluble cellulose ethers has a gelling temperature of from 38 to 60° C., as determined in a 20% by mass aqueous solution.

15. The composition for forming a film according to claim 4, wherein a mixture obtained of the first, second and third water-soluble cellulose ethers has a degree of substitution (DS) of the methoxy groups of from 1.50 to 2.00, and a molar substitution (MS) of the hydroxypropoxy groups of from 0.15 to 0.22.

16. The composition for forming a film according to claim 4, wherein a mixture of the first, second and third water-soluble cellulose ethers has a viscosity at 20° C. of from 3.0 to 15.0 mPa·s, as determined in a 2% by mass aqueous solution.

17. The composition for forming a film according to claim 4, wherein a mixture of the first, second and third water-soluble cellulose ethers has a gelling temperature of from 38 to 60° C., as determined in a 20% by mass aqueous solution.

18. The composition for forming a film according to claim 5, wherein a mixture of the first, second and third water-soluble cellulose ethers has a viscosity at 20° C. of from 3.0 to 15.0 mPa·s, as determined in a 2% by mass aqueous solution.

19. The composition for forming a film according to claim 5, wherein a mixture of the first, second and third water-soluble cellulose ethers has a gelling temperature of from 38 to 60° C., as determined in a 20% by mass aqueous solution.

20. The composition for forming a film according to claim 6, wherein a mixture of the first, second and third water-soluble cellulose ethers has a gelling temperature of from 38 to 60° C., as determined in a 20% by mass aqueous solution.

* * * * *

UNITED STATES PATENT AND TRADEMARK OFFICE
CERTIFICATE OF CORRECTION

| | |
|---|---|
| PATENT NO. | : 11,479,658 B2 |
| APPLICATION NO. | : 17/196213 |
| DATED | : October 25, 2022 |
| INVENTOR(S) | : Matsusue et al. |

It is certified that error appears in the above-identified patent and that said Letters Patent is hereby corrected as shown below:

In the Specification

Column 3, Line 32: Please correct "mPa-s" to read --mPa·s--

Column 5, Line 1: Please correct "(Ia, Ia, Ha)" to read --(Ia, Ia, IIa)--

Column 10, Line 33: Please correct "030" to read --0.07--

Column 11, Line 2: Please correct "mPa's" to read --mPa·s--

Column 12, Line 8: Please correct "IVICR301" to read --MCR301--

Column 12, Line 31: Please correct "PR-33" to read --PR-3J--

Column 12, Line 32: Please correct "PR-33" to read --PR-3J--

Column 12, Line 42: Please correct "1.0 mm/min" to read --10 mm/min--

Signed and Sealed this
Thirtieth Day of May, 2023

Katherine Kelly Vidal
*Director of the United States Patent and Trademark Office*